US008703918B2

(12) United States Patent
Colombatti et al.

(10) Patent No.: US 8,703,918 B2
(45) Date of Patent: Apr. 22, 2014

(54) ISOLATED MONOCLONAL ANTIBODY OR FRAGMENT THEREOF BINDING PROSTATE SPECIFIC MEMBRANE ANTIGEN, CONJUGATES AND USES THEREOF

(75) Inventors: Marco Colombatti, Sant' Anna d'Alfaedo (IT); Giulio Fracasso, Verona (IT); Sara Cingarlini, Verona (IT); Silvana Canevari, Segrate (IT); Mariangela Figini, Milan (IT)

(73) Assignees: Universita' degli Studi di Verona, Verona (IT); Fondazione IRCCS "Instituto Nazionale dei Tumori", Milan (IT); Marco Colombatti, Sant' Anna d'alfaedo (IT)

( * ) Notice: Subject to any disclaimer, the term of this patent is extended or adjusted under 35 U.S.C. 154(b) by 393 days.

(21) Appl. No.: 12/989,316

(22) PCT Filed: Apr. 22, 2009

(86) PCT No.: PCT/IB2009/005326
§ 371 (c)(1),
(2), (4) Date: Oct. 24, 2011

(87) PCT Pub. No.: WO2009/130575
PCT Pub. Date: Oct. 29, 2009

(65) Prior Publication Data
US 2012/0034168 A1  Feb. 9, 2012

(30) Foreign Application Priority Data
Apr. 22, 2008  (IT) .............. TO2008A0313

(51) Int. Cl.
*C07K 16/00* (2006.01)
*C12P 21/08* (2006.01)
*A61K 39/395* (2006.01)
*A61K 39/00* (2006.01)
*G01N 33/53* (2006.01)

(52) U.S. Cl.
USPC ............ 530/387.1; 530/388.1; 530/387.3; 530/391.3; 530/391.7; 424/178.1; 435/7.1

(58) Field of Classification Search
None
See application file for complete search history.

(56) References Cited

FOREIGN PATENT DOCUMENTS

EP  1 726 650  11/2006

OTHER PUBLICATIONS

Bander et al., "Targeted systemic therapy of prostate cancer with a monoclonal antibody to prostate-specific membrane antigen", Seminars in Oncology, 30(5):667-677 (Oct. 2003).
Chignola et al., "Self-potentiation of Ligand-Toxin Conjugates Containing Ricin A Chain Fused with Viral Structures", J. Biol. Chem., 270:23345-51 (1995).
Elsasser-Beile et al., "A new generation of monoclonal and recombinant antibodies against cell-adherent prostate specific membrane antigen for diagnostic and therapeutic targeting of prostate cancer", Prostate, Wiley-Liss, New York, NY, 66:1359-1370 (Jan. 2006).
Fracasso et al., "Anti-tumor effects of toxins targeted t the prostate specific membrane antigen", Prostate, Wiley-Liss, New York, NY, 53(1):9-23 (Sep. 2002).
Goldenberg et al., "Antibody Pretargeting Advances Cancer Radioimmunodetection and Radioimmunotherapy", J. Clin. Oncol., 24:823-834 (2006).
Sodee et al., "Synergistic value of single-photon emission computed tomography/computed tomography fusion to radioimmunoscintigraphic imaging of prostate cancer", Seminars in Nuclear Medicine, Grune and Stratton, Orlando, Florida, 37(1):17-28 (Dec. 2006).
International Search Report for PCT/IB2009/005326 dated Nov. 20, 2009.
Written Opinion for PCT/IB2009/005326 dated Nov. 20, 2009.
International Preliminary Report on Patentability dated Jul. 2, 2010.

*Primary Examiner* — Hong Sang
(74) *Attorney, Agent, or Firm* — Marshall, Gerstein & Borun LLP (57) ABSTRACT

An isolated monoclonal antibody or fragment thereof binding prostate specific membrane antigen (PSMA) preferably in its native form on the surface of tumour cells. A conjugate of the antibody with an active ingredient and modified forms of the antigen-binding antibody fragment are also provided. The complete antibody and the antigen-recognising fragment thereof are used alone or conjugated for the treatment and the diagnosis of tumours or tissues associated to the tumour overexpressing the PSMA antigen, preferably prostatic neoplastic diseases.

14 Claims, 4 Drawing Sheets

Figure 1- Western Blot with moAb D2/B

1 D2/B LNCaP; 2 J591 LNCaP; 3 D2/B PC-3; 4 J591 PC-3

Figure 2 -Western Blot with scFv D2/B

Figure 3- Flow cytometry analysis with D2/B and scFv D2/B in PSMA+ cells.

Figure 4 - Flow cytometry analysis with D2/B and scFv D2/B in PSMA- cells

4.A moAb D2/B

4.B

PSMA- PC-3 Cells scFv D2/B

4.C

Neg CRTL

4.D

Neg CTRL

Figure 5 Comparison of binding to LNCaP (PSMA+) cells of J591, D2/B, and scFv D2/B

Figure 6 In vivo imaging with antibody D2/B linked to the fluorophore Cy5.5

SEQUENCE LISTING

```
<160> NUMBER OF SEQ ID NOS: 6

<210> SEQ ID NO 1
<211> LENGTH: 366
<212> TYPE: DNA
<213> ORGANISM: mus musculus
<220> FEATURE:
<221> NAME/KEY: V_region
<222> LOCATION: (1)..(366)
<223> OTHER INFORMATION: Ab D2/B Variable heavy chain
<220> FEATURE:
<221> NAME/KEY: misc_feature
<222> LOCATION: (97)..(114)
<223> OTHER INFORMATION: CDRH1
<220> FEATURE:
<221> NAME/KEY: misc_feature
<222> LOCATION: (157)..(204)
<223> OTHER INFORMATION: CDRH2
<220> FEATURE:
<221> NAME/KEY: misc_feature
<222> LOCATION: (301)..(336)
<223> OTHER INFORMATION: CDRH3

<400> SEQUENCE: 1
atggccgagg tgaagctcca ggagtcagga cctggcctcg ttaaaccttc tcagtctctg      60
tctctcacct gctctgtcac tggctactcc atcaccagtg gttattactg gaactggatc     120
cggcagtttc caggaaacaa actggagtgg atgggctcca taagtttcga cggtaacaat     180
aactacaacc catctctcag aaatcgaatc tccatcactc gtgacacatc taagaaccag     240
ttttttctga agttgaattc tgtgactact gaagacacag ctacatatta ctgtgcaaga     300
gagggagatt actacggtag tagcttcttt acttactggg gccaagggac tctggtcact     360
gtctcg                                                                366

<210> SEQ ID NO 2
<211> LENGTH: 327
<212> TYPE: DNA
<213> ORGANISM: mus  musculus
<220> FEATURE:
<221> NAME/KEY: V_region
<222> LOCATION: (1)..(327)
<223> OTHER INFORMATION: Ab D2/B variable light chain
<220> FEATURE:
<221> NAME/KEY: misc_feature
<222> LOCATION: (76)..(108)
<223> OTHER INFORMATION: CDRL1
<220> FEATURE:
<221> NAME/KEY: misc_feature
<222> LOCATION: (154)..(174)
<223> OTHER INFORMATION: CDRL2
```

```
<220> FEATURE:
<221> NAME/KEY: misc_feature
<222> LOCATION: (271)..(294)
<223> OTHER INFORMATION: CDRL3

<400> SEQUENCE: 2
gcactcgaca ttgtgatgac tcagtctcca gcttcactgt ctgcatctgt gggagaaact    60
gtcaccctca catgtggagc aagtgagaat atttacggtg cttaaattg tatcagcgg    120 aaacagggaa atctcctca actcctgatc tatggagcaa ccaacttggc agatggcatg    180
tcatcgaggt tcagtggcag cggatctggt agacagtatt ctctcaagat cagtagcctg    240
catcctgacg atgttgcaac gtattactgt caaaatgtgt ttcgtactta cacgttcgga    300 gggggacaa agttggaaat aaaacgg    327

<210> SEQ ID NO 3
<211> LENGTH: 822
<212> TYPE: DNA
<213> ORGANISM: mus musculus
<220> FEATURE:
<221> NAME/KEY: CDS
<222> LOCATION: (1)..(822)
<223> OTHER INFORMATION: scFv D2/B
<220> FEATURE:
<221> NAME/KEY: V_region
<222> LOCATION: (1)..(366)
<223> OTHER INFORMATION: scFv D2/B variable heavy chain
<220> FEATURE:
<221> NAME/KEY: V_region
<222> LOCATION: (415)..(741)
<223> OTHER INFORMATION: scFv D2/B variable light chain

<400> SEQUENCE: 3 atg gcc gag gtg aag ctc cag gag tca gga cct ggc ctc gtt aaa cct     48
Met Ala Glu Val Lys Leu Gln Glu Ser Gly Pro Gly Leu Val Lys Pro
1               5                   10                  15 tct cag tct ctg tct ctc acc tgc tct gtc act ggc tac tcc atc acc     96
Ser Gln Ser Leu Ser Leu Thr Cys Ser Val Thr Gly Tyr Ser Ile Thr
            20                  25                  30 agt ggt tat tac tgg aac tgg atc cgg cag ttt cca gga aac aaa ctg    144
Ser Gly Tyr Tyr Trp Asn Trp Ile Arg Gln Phe Pro Gly Asn Lys Leu
        35                  40                  45 gag tgg atg ggc tcc ata agt ttc gac ggt aac aat aac tac aac cca    192
Glu Trp Met Gly Ser Ile Ser Phe Asp Gly Asn Asn Asn Tyr Asn Pro
    50                  55                  60 tct ctc aga aat cga atc tcc atc act cgt gac aca tct aag aac cag    240
Ser Leu Arg Asn Arg Ile Ser Ile Thr Arg Asp Thr Ser Lys Asn Gln
65                  70                  75                  80 ttt ttt ctg aag ttg aat tct gtg act act gaa gac aca gct aca tat    288
Phe Phe Leu Lys Leu Asn Ser Val Thr Thr Glu Asp Thr Ala Thr Tyr
                85                  90                  95 tac tgt gca aga gag gga gat tac tac ggt agc agc ttc ttt act tac    336
Tyr Cys Ala Arg Glu Gly Asp Tyr Tyr Gly Ser Ser Phe Phe Thr Tyr
            100                 105                 110 tgg ggc caa ggg act ctg gtc act gtc tcg agt ggt gga ggc ggt tca    384
Trp Gly Gln Gly Thr Leu Val Thr Val Ser Ser Gly Gly Gly Gly Ser
        115                 120                 125 ggc gga ggt ggc tct gga ggt ggc ggt agt gca ctc gac att gtg atg    432
Gly Gly Gly Gly Ser Gly Gly Gly Gly Ser Ala Leu Asp Ile Val Met
    130                 135                 140 act cag tct cca gct tca ctg tct gca tct gtg gga gaa act gtc acc    480
Thr Gln Ser Pro Ala Ser Leu Ser Ala Ser Val Gly Glu Thr Val Thr
145                 150                 155                 160 ctc aca tgt gga gca agt gag aat att tac ggt gct tta aat tgg tat    528
Leu Thr Cys Gly Ala Ser Glu Asn Ile Tyr Gly Ala Leu Asn Trp Tyr
```

```
Leu Thr Cys Gly Ala Ser Glu Asn Ile Tyr Gly Ala Leu Asn Trp Tyr
                165                 170                 175 cag cgg aaa cag gga aaa tct cct caa ctc ctg atc tat gga gca acc      576
Gln Arg Lys Gln Gly Lys Ser Pro Gln Leu Leu Ile Tyr Gly Ala Thr
            180                 185                 190 aac ttg gca gat ggc atg tca tcg agg ttc agt ggc agc gga tct ggt      624
Asn Leu Ala Asp Gly Met Ser Ser Arg Phe Ser Gly Ser Gly Ser Gly
        195                 200                 205 aga cag tat tct ctc aag atc agt agc ctg cat cct gac gat gtt gca      672
Arg Gln Tyr Ser Leu Lys Ile Ser Ser Leu His Pro Asp Asp Val Ala
    210                 215                 220 acg tat tac tgt caa aat gtg ttt cgt act tac acg ttc gga ggg ggg      720
Thr Tyr Tyr Cys Gln Asn Val Phe Arg Thr Tyr Thr Phe Gly Gly Gly
225                 230                 235                 240 aca aag ttg gaa ata aaa cgg gcg gcc gca cat cat cat cac cat cac      768
Thr Lys Leu Glu Ile Lys Arg Ala Ala Ala His His His His His His
                245                 250                 255 ggg gcc gca gaa caa aaa ctc atc tca gaa gag gat ctg aat ggg gcc      816
Gly Ala Ala Glu Gln Lys Leu Ile Ser Glu Glu Asp Leu Asn Gly Ala
            260                 265                 270 gca tag                                                              822
Ala

<210> SEQ ID NO 4
<211> LENGTH: 273
<212> TYPE: PRT
<213> ORGANISM: mus musculus

<400> SEQUENCE: 4

Met Ala Glu Val Lys Leu Gln Glu Ser Gly Pro Gly Leu Val Lys Pro
1               5                   10                  15

Ser Gln Ser Leu Ser Leu Thr Cys Ser Val Thr Gly Tyr Ser Ile Thr
            20                  25                  30

Ser Gly Tyr Tyr Trp Asn Trp Ile Arg Gln Phe Pro Gly Asn Lys Leu
        35                  40                  45

Glu Trp Met Gly Ser Ile Ser Phe Asp Gly Asn Asn Asn Tyr Asn Pro
    50                  55                  60

Ser Leu Arg Asn Arg Ile Ser Ile Thr Arg Asp Thr Ser Lys Asn Gln
65                  70                  75                  80

Phe Phe Leu Lys Leu Asn Ser Val Thr Thr Glu Asp Thr Ala Thr Tyr
                85                  90                  95

Tyr Cys Ala Arg Glu Gly Asp Tyr Tyr Gly Ser Ser Phe Phe Thr Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Ala Leu Asp Ile Val Met
    130                 135                 140

Thr Gln Ser Pro Ala Ser Leu Ser Ala Ser Val Gly Glu Thr Val Thr
145                 150                 155                 160

Leu Thr Cys Gly Ala Ser Glu Asn Ile Tyr Gly Ala Leu Asn Trp Tyr
                165                 170                 175

Gln Arg Lys Gln Gly Lys Ser Pro Gln Leu Leu Ile Tyr Gly Ala Thr
            180                 185                 190

Asn Leu Ala Asp Gly Met Ser Ser Arg Phe Ser Gly Ser Gly Ser Gly
        195                 200                 205

Arg Gln Tyr Ser Leu Lys Ile Ser Ser Leu His Pro Asp Asp Val Ala
    210                 215                 220
```

```
Thr Tyr Tyr Cys Gln Asn Val Phe Arg Thr Tyr Thr Phe Gly Gly Gly
225                 230                 235                 240

Thr Lys Leu Glu Ile Lys Arg Ala Ala Ala His His His His His His
                245                 250                 255

Gly Ala Ala Glu Gln Lys Leu Ile Ser Glu Glu Asp Leu Asn Gly Ala
            260                 265                 270

Ala

<210> SEQ ID NO 5
<211> LENGTH: 1830
<212> TYPE: DNA
<213> ORGANISM: Artificial sequence
<220> FEATURE:
<223> OTHER INFORMATION: conjugate between mouse and bacteria
<220> FEATURE:
<221> NAME/KEY: CDS
<222> LOCATION: (1)..(1830)
<223> OTHER INFORMATION: scFv D2/B-PE40
<220> FEATURE:
<221> NAME/KEY: V_region
<222> LOCATION: (1)..(738)
<223> OTHER INFORMATION: scFv D2/B variable heavy and light chain region
<220> FEATURE:
<221> NAME/KEY: misc_feature
<222> LOCATION: (739)..(1830)
<223> OTHER INFORMATION: PE40 Toxin Sequence

<400> SEQUENCE: 5 atg gcc gag gtg aag ctc cag gag tca gga cct ggc ctc gtt aaa cct      48
Met Ala Glu Val Lys Leu Gln Glu Ser Gly Pro Gly Leu Val Lys Pro
1               5                   10                  15 tct cag tct ctg tct ctc acc tgc tct gtc act ggc tac tcc atc acc      96
Ser Gln Ser Leu Ser Leu Thr Cys Ser Val Thr Gly Tyr Ser Ile Thr
            20                  25                  30 agt ggt tat tac tgg aac tgg atc cgg cag ttt cca gga aac aaa ctg     144
Ser Gly Tyr Tyr Trp Asn Trp Ile Arg Gln Phe Pro Gly Asn Lys Leu
        35                  40                  45 gag tgg atg ggc tcc ata agt ttc gac ggt aac aat aac tac aac cca     192
Glu Trp Met Gly Ser Ile Ser Phe Asp Gly Asn Asn Asn Tyr Asn Pro
    50                  55                  60 tct ctc aga aat cga atc tcc atc act cgt gac aca tct aag aac cag     240
Ser Leu Arg Asn Arg Ile Ser Ile Thr Arg Asp Thr Ser Lys Asn Gln
65                  70                  75                  80 ttt ttt ctg aag ttg aat tct gtg act act gaa gac aca gct aca tat     288
Phe Phe Leu Lys Leu Asn Ser Val Thr Thr Glu Asp Thr Ala Thr Tyr
                85                  90                  95 tac tgt gca aga gag gga gat tac tac ggt agc agc ttc ttt act tac     336
Tyr Cys Ala Arg Glu Gly Asp Tyr Tyr Gly Ser Ser Phe Phe Thr Tyr
            100                 105                 110 tgg ggc caa ggg act ctg gtc act gtc tcg agt ggt gga ggc ggt tca     384
Trp Gly Gln Gly Thr Leu Val Thr Val Ser Ser Gly Gly Gly Gly Ser
        115                 120                 125 ggc gga ggt ggc tct gga ggt ggc ggt agt gca ctc gac att gtg atg     432
Gly Gly Gly Gly Ser Gly Gly Gly Gly Ser Ala Leu Asp Ile Val Met
    130                 135                 140 act cag tct cca gct tca ctg tct gca tct gtg gga gaa act gtc acc     480
Thr Gln Ser Pro Ala Ser Leu Ser Ala Ser Val Gly Glu Thr Val Thr
145                 150                 155                 160 ctc aca tgt gga gca agt gag aat att tac ggt gct tta aat tgg tat     528
Leu Thr Cys Gly Ala Ser Glu Asn Ile Tyr Gly Ala Leu Asn Trp Tyr
                165                 170                 175
```

```
                                                             -continued cag cgg aaa cag gga aaa tct cct caa ctc ctg atc tat gga gca acc          576
Gln Arg Lys Gln Gly Lys Ser Pro Gln Leu Leu Ile Tyr Gly Ala Thr
        180                 185                 190 aac ttg gca gat ggc atg tca tcg agg ttc agt ggc agc gga tct ggt          624
Asn Leu Ala Asp Gly Met Ser Ser Arg Phe Ser Gly Ser Gly Ser Gly
            195                 200                 205 aga cag tat tct ctc aag atc agt agc ctg cat cct gac gat gtt gca          672
Arg Gln Tyr Ser Leu Lys Ile Ser Ser Leu His Pro Asp Asp Val Ala
    210                 215                 220 acg tat tac tgt caa aat gtg ttt cgt act tac acg ttc gga ggg ggg          720
Thr Tyr Tyr Cys Gln Asn Val Phe Arg Thr Tyr Thr Phe Gly Gly Gly
225                 230                 235                 240 aca aag ttg gaa ata aaa gct ttc ggc ggc agc ctg gcg ctg acc              768
Thr Lys Leu Glu Ile Lys Ala Phe Gly Gly Ser Leu Ala Ala Leu Thr
                245                 250                 255 gcg cac cag gct tgc cac ctg ccg ctg gag act ttc acc cgt cat cgc          816
Ala His Gln Ala Cys His Leu Pro Leu Glu Thr Phe Thr Arg His Arg
            260                 265                 270 cag ccg cgc ggc tgg gaa caa ctg gag cag tgc ggc tat ccg gtg cag          864
Gln Pro Arg Gly Trp Glu Gln Leu Glu Gln Cys Gly Tyr Pro Val Gln
    275                 280                 285 cgg ctg gtc gcc ctc tac ctg gcg gcg cgg ctg tcg tgg aac cag gtc          912
Arg Leu Val Ala Leu Tyr Leu Ala Ala Arg Leu Ser Trp Asn Gln Val
290                 295                 300 gac cag gtg atc cgc aac gcc ctg gcc agc ccc ggc agc ggc ggc gac          960
Asp Gln Val Ile Arg Asn Ala Leu Ala Ser Pro Gly Ser Gly Gly Asp
305                 310                 315                 320 ctg ggc gaa gcg atc cgc gag cag ccg gag cag gcc cgt ctg gcc ctg         1008
Leu Gly Glu Ala Ile Arg Glu Gln Pro Glu Gln Ala Arg Leu Ala Leu
                325                 330                 335 acc ctg gcc gcc gcc gag agc gag cgc ttc gtc cgg cag ggc acc ggc         1056
Thr Leu Ala Ala Ala Glu Ser Glu Arg Phe Val Arg Gln Gly Thr Gly
            340                 345                 350 aac gac gag gcc ggc gcg gcc aac gcc gac gtg gtg agc ctg acc tgc         1104
Asn Asp Glu Ala Gly Ala Ala Asn Ala Asp Val Val Ser Leu Thr Cys
    355                 360                 365 ccg gtc gcc gcc ggt gaa tgc gcg ggc ccg gcg gac agc ggc gac gcc         1152
Pro Val Ala Ala Gly Glu Cys Ala Gly Pro Ala Asp Ser Gly Asp Ala
370                 375                 380 ctg ctg gag cgc aac tat ccc act ggc gcg gag ttc ctc ggc gac ggc         1200
Leu Leu Glu Arg Asn Tyr Pro Thr Gly Ala Glu Phe Leu Gly Asp Gly
385                 390                 395                 400 ggc gac gtc agc ttc agc acc cgc ggc acg cag aac tgg acg gtg gag         1248
Gly Asp Val Ser Phe Ser Thr Arg Gly Thr Gln Asn Trp Thr Val Glu
                405                 410                 415 cgg ctg ctc cag gcg cac cgc caa ctg gag gag cgc ggc tat gtg ttc         1296
Arg Leu Leu Gln Ala His Arg Gln Leu Glu Glu Arg Gly Tyr Val Phe
            420                 425                 430 gtc ggc tac cac ggc acc ttc ctc gaa gcg gcg caa agc atc gtc ttc         1344
Val Gly Tyr His Gly Thr Phe Leu Glu Ala Ala Gln Ser Ile Val Phe
    435                 440                 445 ggc ggg gtg cgc gcg cgc agc cag gac ctc gac gcg atc tgg cgc ggt         1392
Gly Gly Val Arg Ala Arg Ser Gln Asp Leu Asp Ala Ile Trp Arg Gly
450                 455                 460 ttc tat atc gcc ggc gat ccg gcg ctg gcc tac ggc tac gcc cag gac         1440
Phe Tyr Ile Ala Gly Asp Pro Ala Leu Ala Tyr Gly Tyr Ala Gln Asp
465                 470                 475                 480 cag gaa ccc gac gca cgc ggc cgg atc cgc aac ggt gcc ctg ctg cgg         1488
Gln Glu Pro Asp Ala Arg Gly Arg Ile Arg Asn Gly Ala Leu Leu Arg
                485                 490                 495
```

-continued

| | | |
|---|---|---|
| gtc tat gtg ccg cgc tcg agc ctg ccg ggc ttc tac cgc acc agc ctg<br>Val Tyr Val Pro Arg Ser Ser Leu Pro Gly Phe Tyr Arg Thr Ser Leu<br>500 505 510 | | 1536 |
| acc ctg gcc gcg ccg gag gcg gcg ggc gag gtc gaa cgg ctg atc ggc<br>Thr Leu Ala Ala Pro Glu Ala Ala Gly Glu Val Glu Arg Leu Ile Gly<br>515 520 525 | | 1584 |
| cat ccg ctg ccg ctg cgc ctg gac gcc atc acc ggc ccc gag gag gaa<br>His Pro Leu Pro Leu Arg Leu Asp Ala Ile Thr Gly Pro Glu Glu Glu<br>530 535 540 | | 1632 |
| ggc ggg cgc ctg gag acc att ctc ggc tgg ccg ctg gcc gag cgc acc<br>Gly Gly Arg Leu Glu Thr Ile Leu Gly Trp Pro Leu Ala Glu Arg Thr<br>545 550 555 560 | | 1680 |
| gtg gtg att ccc tcg gcg atc ccc acc gac ccg cgc aac gtc ggc ggc<br>Val Val Ile Pro Ser Ala Ile Pro Thr Asp Pro Arg Asn Val Gly Gly<br>565 570 575 | | 1728 |
| gac ctc gac ccg tcc agc atc ccc gac aag gaa cag gcg atc agc gcc<br>Asp Leu Asp Pro Ser Ser Ile Pro Asp Lys Glu Gln Ala Ile Ser Ala<br>580 585 590 | | 1776 |
| ctg ccg gac tac gcc agc cag ccc ggc aaa ccg ccg cgc gag gac ctg<br>Leu Pro Asp Tyr Ala Ser Gln Pro Gly Lys Pro Pro Arg Glu Asp Leu<br>595 600 605 | | 1824 |
| aag taa<br>Lys | | 1830 |

<210> SEQ ID NO 6
<211> LENGTH: 609
<212> TYPE: PRT
<213> ORGANISM: Artificial sequence
<220> FEATURE:
<223> OTHER INFORMATION: conjugate between mouse and bacteria
<220> FEATURE:
<221> NAME/KEY: V_region
<222> LOCATION: (1)..(738)
<223> OTHER INFORMATION: scFv D2/B variable heavy and light chain region
<220> FEATURE:
<221> NAME/KEY: misc_feature
<222> LOCATION: (739)..(1830)
<223> OTHER INFORMATION: PE40 Toxin Sequence

<400> SEQUENCE: 6

Met Ala Glu Val Lys Leu Gln Glu Ser Gly Pro G

```
                    165                 170                 175
Gln Arg Lys Gln Gly Lys Ser Pro Gln Leu Leu Ile Tyr Gly Ala Thr
            180                 185                 190

Asn Leu Ala Asp Gly Met Ser Ser Arg Phe Ser Gly Ser Gly Ser Gly
        195                 200                 205

Arg Gln Tyr Ser Leu Lys Ile Ser Ser Leu His Pro Asp Asp Val Ala
    210                 215                 220

Thr Tyr Tyr Cys Gln Asn Val Phe Arg Thr Tyr Thr Phe Gly Gly Gly
225                 230                 235                 240

Thr Lys Leu Glu Ile Lys Ala Phe Gly Gly Ser Leu Ala Ala Leu Thr
            245                 250                 255

Ala His Gln Ala Cys His Leu Pro Leu Glu Thr Phe Thr Arg His Arg
        260                 265                 270

Gln Pro Arg Gly Trp Glu Gln Leu Glu Gln Cys Gly Tyr Pro Val Gln
    275                 280                 285

Arg Leu Val Ala Leu Tyr Leu Ala Ala Arg Leu Ser Trp Asn Gln Val
    290                 295                 300

Asp Gln Val Ile Arg Asn Ala Leu Ala Ser Pro Gly Ser Gly Gly Asp
305                 310                 315                 320

Leu Gly Glu Ala Ile Arg Glu Gln Pro Glu Gln Ala Arg Leu Ala Leu
            325                 330                 335

Thr Leu Ala Ala Ala Glu Ser Glu Arg Phe Val Arg Gln Gly Thr Gly
        340                 345                 350

Asn Asp Glu Ala Gly Ala Ala Asn Ala Asp Val Val Ser Leu Thr Cys
    355                 360                 365

Pro Val Ala Ala Gly Glu Cys Ala Gly Pro Ala Asp Ser Gly Asp Ala
370                 375                 380

Leu Leu Glu Arg Asn Tyr Pro Thr Gly Ala Glu Phe Leu Gly Asp Gly
385                 390                 395                 400

Gly Asp Val Ser Phe Ser Thr Arg Gly Thr Gln Asn Trp Thr Val Glu
            405                 410                 415

Arg Leu Leu Gln Ala His Arg Gln Leu Glu Glu Arg Gly Tyr Val Phe
        420                 425                 430

Val Gly Tyr His Gly Thr Phe Leu Glu Ala Ala Gln Ser Ile Val Phe
    435                 440                 445

Gly Gly Val Arg Ala Arg Ser Gln Asp Leu Asp Ala Ile Trp Arg Gly
    450                 455                 460

Phe Tyr Ile Ala Gly Asp Pro Ala Leu Ala Tyr Gly Tyr Ala Gln Asp
465                 470                 475                 480

Gln Glu Pro Asp Ala Arg Gly Arg Ile Arg Asn Gly Ala Leu Leu Arg
            485                 490                 495

Val Tyr Val Pro Arg Ser Ser Leu Pro Gly Phe Tyr Arg Thr Ser Leu
        500                 505                 510

Thr Leu Ala Ala Pro Glu Ala Ala Gly Glu Val Glu Arg Leu Ile Gly
    515                 520                 525

His Pro Leu Pro Leu Arg Leu Asp Ala Ile Thr Gly Pro Glu Glu Glu
    530                 535                 540

Gly Gly Arg Leu Glu Thr Ile Leu Gly Trp Pro Leu Ala Glu Arg Thr
545                 550                 555                 560

Val Val Ile Pro Ser Ala Ile Pro Thr Asp Pro Arg Asn Val Gly Gly
            565                 570                 575

Asp Leu Asp Pro Ser Ser Ile Pro Asp Lys Glu Gln Ala Ile Ser Ala
        580                 585                 590
```

-continued

```
Leu Pro Asp Tyr Ala Ser Gln Pro Gly Lys Pro Pro Arg Glu Asp Leu
        595                 600                 605
Lys
```

ISOLATED MONOCLONAL ANTIBODY OR FRAGMENT THEREOF BINDING PROSTATE SPECIFIC MEMBRANE ANTIGEN, CONJUGATES AND USES THEREOF

CROSS-REFERENCE TO RELATED APPLICATIONS

This is the U.S. national phase application of International Application No. PCT/IB2009/005326, filed Apr. 22, 2009, which claims the benefit of Italian Patent Application No. TO2008A000313, filed Apr. 22, 2008.

INCORPORATION BY REFERENCE OF MATERIALS SUBMITTED ELECTRONICALLY

This application contains, as a separate part of disclosure, a Sequence Listing in computer-readable form (filename: 45853 SeqListing.txt; 23,667 byte-ASCII text file; created Jan. 2, 2013) which is incorporated by reference in its entirety.

TECHNICAL FIELD

The present invention relates to monoclonal antibodies and antigen-binding fragments thereof defined as scFV hereinafter, as reagents for the diagnosis and treatment of prostate tumours and the eradication/detection of cells expressing high levels of prostate specific membrane antigen, referred to as PSMA hereinafter.

Prostate cancer is the most frequent form of cancer in males (followed by lung cancer) and represents the second cause of death due to tumour.

Upon onset, prostate cancer is an organ-confined tumour; the surgical removal of the prostate and seminal vesicles and radiotherapy are effective in the treatment of this form of tumour.

However, when the tumour is diagnosed in an advanced stage and in cases in which the disease evolves into more aggressive metastatic and androgen-independent forms, the use of different pharmacological approaches is ineffective.

In these cases, new therapeutic strategies based on passive immunotherapy and specific monoclonal antibodies (moAbs) may therefore result useful to treat these advanced and metastatic prostate cancer forms.

Tumour associated antigens (TAAs), i.e. molecules which are overexpressed by the neoplastic tissue and may potentially be used as targets for immunological therapy, need to be identified to apply this therapy.

Recent studies suggest that prostate specific membrane antigen (PSMA) may represent the ideal antigen target in prostate cancer due to its features.

PSMA is a glycoprotein of about 100 kDa with a short intracellular domain (amino acids 1-18), a transmembrane domain (amino acids 19-43) and an extracellular domain (amino acids 44-750). PSMA is expressed in both normal and cancerous epithelial prostate cells, although with an expression level which is considerably increased in prostate cancer; this level tends to increase with the severeness and progression of the disease.

On the other side, normal extraprostatic tissues, such as for instance the proximal tubules of the kidney, the duodenum and the colon have a limited expression of the PSMA antigen.

As a target of antitumoral immunotherapies, PSMA has the advantage of being mainly expressed in the prostate and being a transmembrane protein present on the cell surface and internalised from the cell membrane through endocytic vesicles coated with clathrin. These features allow to use PSMA for the therapy with immunotoxins. Advantageously, the binding of antibodies or antibody fragments to the extracellular domain promotes this endocytosis process.

BACKGROUND ART

Many PSMA-binding monoclonal antibodies are known. For instance, 7E11, which has been approved by the FDA for the study of metastases expressing PSMA, is a monoclonal antibody that binds the intracellular portion of PSMA. Unfortunately, however, 7E11 does not bind viable cells, but only necrotic or apoptotic cells within a tumour mass.

Monoclonal antibodies such as J591, J415, J533 and E99 have subsequently been produced. These antibodies recognise epitopes on the extracellular domain of PSMA and therefore bind viable cells.

J591 has in particular been used for several in vitro studies and in animal models both diagnostically and therapeutically and is still under clinical experimental study.

Finally, EP1726650 discloses another monoclonal antibody and an scFv fragment thereof which binds to PSMA.

Hereinafter, the term "fragment of the antibody binding the antigen" indicates one or more fragments of this antibody which maintains/maintain the ability to specifically bind PSMA.

BRIEF DESCRIPTION OF THE DRAWINGS

For a better understanding of the present invention, it is now also described with reference to the accompanying figures, in which:

FIG. 3 a-d show cytofluorimetric analyses of D2/B and scFv D2/B on PSMA+ cells;

FIG. 4 a-d show cytofluorimetric analyses of D2/B and scFv D2/B on PSMA− cells;

DISCLOSURE OF INVENTION

It is an object of the present invention to find new monoclonal antibodies for the treatment of prostate cancer, which are selective for tumour cells, allow an earlier and more accurate diagnosis and represent therapeutic options which truly allow to affect the biology of the disease in an advanced and metastatic stage so as to more effectively cope with an ever increasing social and medical problem that has uncertain solution perspectives with current therapeutical measures.

According to the present invention, this object is achieved by an isolated monoclonal antibody or an antigen-binding fragment thereof according to claim 1, a conjugate thereof according to claim 5, a pharmaceutical composition comprising the same according to claim 8. The use of the antibody and of the fragment thereof, of the conjugate and of the pharmaceutical composition is also provided according to claim 11.

DETAILED DESCRIPTION OF THE INVENTION

On prostate cells PSMA is expressed with a specific tertiary and quaternary structure and the antibodies obtained with an isolated and denatured PSMA do not effectively recognise the PSMA expressed on tumour cells. The antibodies and fragments thereof according to the present invention advantageously bind PSMA in its native form with a high affinity and may therefore be effectively used both in therapy and diagnostics. In particular, the monoclonal antibodies and the fragments thereof according to the invention selectively bind PSMA therefore reducing the side effects of a non-selective therapy.

The used antibody fragments are single chain antibody fragments (scFv) which have a smaller size and a lower immunogenicity with respect to the corresponding antibody. However, in virtue of the small size and the lower affinity for the antigen, they have shown an increase of the permeability in the microcirculation and a better interaction with the antigen in the binding site of the antibody.

The monoclonal antibodies or the fragments thereof comprise a peculiar nucleotide and amino acid sequence at the variable regions VH and VK which determine the specificity and affinity thereof. The nucleotide sequences of the moAb D2/B and of the scFv fragment thereof are indicated as SEQ ID NO: 1, 2, 3, 4. The specified sequence encodes an antibody fragment that has a good binding ability to the PSMA target antigen.

The monoclonal antibody or fragment thereof as disclosed above may be conjugated with an active ingredient to obtain compounds which may be used for radioimmunotherapy or imaging or also recombinant immunotoxins.

The active ingredient is preferably a labelling agent, more preferably a radionuclide selected among $^{188}$Re, $^{131}$I, $^{125}$I, $^{123}$I, $^{187}$Re, $^{111}$In, $^{90}$Y, $^{99m}$Tc, $^{177}$Lu, or fluorescent nanoparticles.

As an alternative, the monoclonal antibody or fragment thereof may be conjugated with a cytotoxic agent, preferably selected among PE40, ricin A chain, diantin, saporin.

Finally, the monoclonal antibody or fragment thereof may be conjugated with biotin to exploit the high affinity of the avidin-biotin interaction or with other molecular pairs that allow multiple-step therapeutic protocols. In particular, the conjugate with biotin may be applied in targeting techniques in the case of treatments which include the use of radioisotopes. Namely, various preclinical studies have highlighted the superiority of pretargeting with respect to direct targeting; for instance Goldenberg D. M. et al. (J. Clin. Oncol., 24:823-834, 2006).

It has been shown that the administration of a conjugate with the antibody according to the invention or of a fragment thereof with biotin, before the administration of a radiopharmaceutical (streptavidin and then radiolabelled biotin) allows a better distribution of the radiopharmaceutical at the tumour site thus reducing the side effects.

The monoclonal antibody, the fragments and conjugates thereof may be formulated in pharmaceutical compositions with appropriate excipients and may be used for the preparation of a medicament for the treatment or diagnosis of tumour tissues overexpressing the PSMA antigen, a tumour, preferably prostate tumour.

The procedure to obtain monoclonal antibodies is as follows:

Balb/c mice are immunised, the cells from the animal's spleen are fused with hybridoma cells, the resulting cells are selected in HAT medium, polyclonal hybridomas recognising the target antigen are identified, cloned and newly characterised to asses specificity/affinity of the now monoclonal hybridomas, which are finally adapted to grow in HAT-free medium. The antibodies are then purified from the culture medium of the hybridoma by means of standard biochemical techniques (affinity chromatography).

Further features of the present invention will result from the following disclosure of some embodiments given by mere way of non-limitative illustration.

EXAMPLES

The monoclonal antibodies and the scFv of the invention have been characterised by flow cytofluorimetry and Western blot on the following cell lines of human PCa, provided by the ATCC (American Type Colture Collection, Rockville, Md.): lymphonodal metastases of PCa (LNCaP), brain metastases of PCa (DU145), bone metastases of PCa (PC-3). These cell lines have been maintained in RPMI 1640 enriched with 10% foetal bovine serum (FBS), 2 mM glutamine, 100 U/ml penicillin and streptomycin. The incubation temperature was 37° C. and the $CO_2$ concentration was 5%. The cells were split 2-3 times per week, detaching them with a 0.02% EDTA/PBS or 0.02% EDTA and 0.05% trypsin/PBS solution.

Hereinafter reference will be made to antibodies according to the invention as "D2/B" and "scFv D2/B".

Example 1

Preparation of moAbs

The antibody was obtained following immunization of Balb/c mice with plasma membrane fractions of cells expressing the PSMA antigen and with the recombinant form of PSMA, following established protocols exploiting the hybridoma technology. Spleen cell populations containing B lymphocytes of immunized animals were fused with myeloma cells. The obtained hybridomas, cloned by limiting dilution and characterized to evaluate specificity and affinity, were grown in an appropriate serum free medium. The antibodies are purified from the culture supernatant by affinity chromatography.

Example 2

ELISA Assay

The Enzyme-Linked Immunosorbent Assay (ELISA) is a technique utilized to detect the presence of a molecule by its reactivity with specific antibodies.

This assay was used to determine the isotype of the anti-PSMA moAbs previously obtained. The kit used (Hybridoma Subisotyping Kit, Calbiochem) has allowed the identification of the antibody isotype among the IgG1, IgG2, IgG2b, IgG3, IgM and IgA subclasses; the procedure of the assay is described in the technical information sheet attached to the ELISA kit used.

The results, reported in Tab. 1 show that antibody D2/B is an IgG1; row number 2 of the table (IgG1) shows an absorbance value of 4.0, as opposed to a negative control (culture medium only) of 0.8. The absorbance values of D2/B for the other IgG subclasses correspond to the negative control value. As a positive control in the assay we used murine serum which, as evidenced from data reported in column number 3, contains all immunoglobulin isotypes.

TABLE 1

|       | D2/B | Negative control | Mouse serum |
|-------|------|------------------|-------------|
| IgM   | 0.56 | 0.54             | 2.36        |
| IgG1  | 4.00 | 0.81             | 1.75        |
| IgG2a | 0.41 | 0.32             | 2.42        |

TABLE 1-continued

|  | D2/B | Negative control | Mouse serum |
|---|---|---|---|
| IgG2b | 0.30 | 0.25 | 1.84 |
| IgG3 | 0.30 | 0.28 | 1.24 |
| IgA | 0.25 | 0.23 | 0.18 |

Example 3

From Monoclonal Antibody to the D2/B scFv Fragment and its Production

After extraction of the total RNA of hybridoma D2/B with TRIzol (Gibco), cDNA was synthesized using the Superscript cDNA Synthesis kit (Invitrogen). Using appropriate pairs of reverse and forward primers and PCR we have identified the primer combinations able to amplify the variable VH and Vk regions of the D2/B moAb, the optimal combinations were identified and the VH and Vk regions were cloned into a plasmidic vector appending a 6-His tag to the protein N-terminus. Sequencing of the vector has allowed identification of VH and Vk sequences (SEQ ID 1, 2).

Production of scFv D2/B takes place in *E. Coli* cells (strain HB2151) grown at 37° C. with stirring (225 rpm) in medium 2×TY additioned with ampicillin 100 µg/ml, glucose 0.1% and the bacteria were induced at an O.D. of 0.8 (600 nm) with a final concentration of 1 mM IPTG for 3 h at 37° C. The cells were harvested by centrifugation at 5000 rpm at 4° C. for 10 min and exposed for 1 h to Tris-HCl 30 mM pH=8.0+EDTA 1 mM+sucrose 20%; the supernatant (containing the periplasmic fraction) is collected and the scFv D2/B is purified by chromatography using a NiNTA (Novagen) matrix eluting with Tris 20 mM pH=8.0+250 mM Imidazole buffer.

Purity of the protein was evaluated by SDS-PAGE.

Example 4

Western Blotting

To verify the recognition potential of D2/B antibody in Western blots an SDS-PAGE (10% polyacrylamide) of PSMA+ LNCaP cells and of PSMA− PC-3 cells was carried out. Cell lysis was performed by sonication of cells resuspended in a solution of 20 mM Tris, 150 mM NaCl pH 8.0 containing 1% Triton X-100 and protease inhibitors (Complete Protease Inhibitor Cocktail, Roche). Slots were loaded with 20 µl lysate corresponding to approx. 100 µg total proteins; the SDS-PAGE was carried out according to the protocol described by Laemmli. Subsequently the proteins separated by gel electrophoresis were transferred to a nitrocellulose membrane by applying an electric field (established procedure, Western blot).

To verify PSMA antigen recognition by the D2/B antibody the nitrocellulose membrane was incubated o.n. at 4° C. with gentle agitation in the presence of the primary antibody D2/B or of the control antibody J591, both used at the concentration of 10-20 µg/ml in a 5% solution of defatted milk. Excess antibody was eliminated by 4 washings using TEST buffer.

A secondary anti-mouse antibody conjugated to HRP and diluted 1:1000 in 5% defatted milk in TBST was then used; incubation lasted 1 h at r.t. with gentle agitation.

After 3 washings in TBST and 1 washing in PBS, the signal was detected by a chemiluminescent reaction (ECL Amersham Biosciences, UK).

Figure 1:
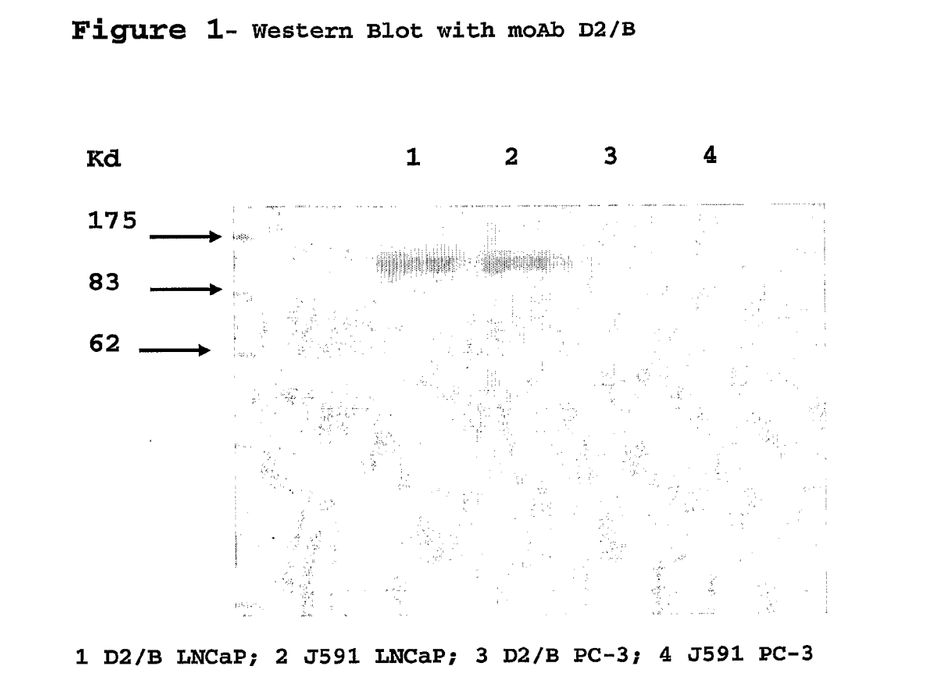
FIG. 1 shows a Western blot performed on a lysate of LNCaP (PSMA+) and PC-3 (PSMA−) cells, using moAb D2/B and antibody J591 (already widely disclosed in the literature) as a control.

FIG. 1 shows a Western blotting carried out with a lysate of LNCaP (PSMA+) and PC-3 (PSMA−) cells, using as a positive control the antibody J591, already described in the literature; as shown in the Figure the antibody D2/B is able to recognize the antigen present in the cell lysate as well as the antibody J591 (lanes 1 and 2, respectively). It can also be appreciated that no signal can be observed using a lysate of antigen negative cells (PC-3) (lanes 3 and 4 for D2/B and J591 antibody, respectively).

Figure 2:
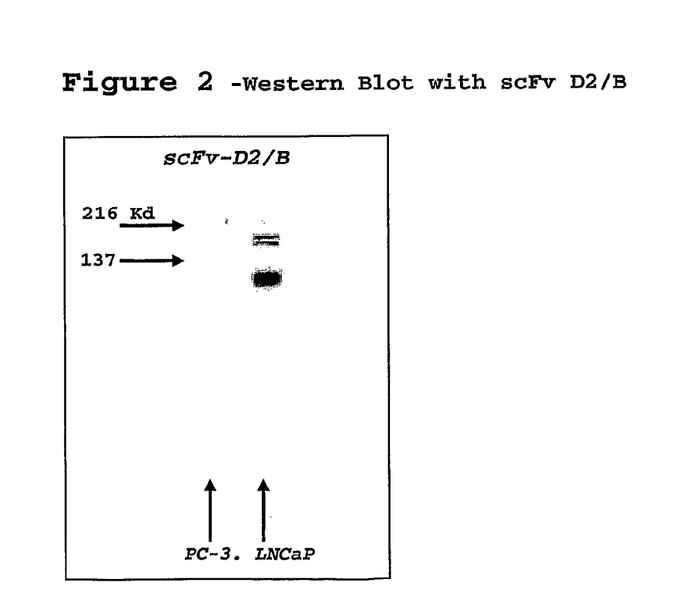
FIG. 2 shows a Western blot performed on a lysate of LNCaP (PSMA+) cells and PC-3 cells, which do not express the PSMA antigenic target, using scFv D2/B.

Likewise, the recognition ability of the antibody scFv D2/B was evaluated in Western blot using the same cell lysates as above but revealing the binding with a rabbit anti-myc tag antibody (Sigma) followed by an anti-rabbit HRP-conjugated antibody (Sigma). The scFv D2/B detects PSMA in the LNCaP cell lysates but no signal is observed with PC-3 cell lysates, lacking the antigenic target PSMA (FIG. 2).

Example 5

Immunofluorescence

LNCaP cells (PSMA+) were grown on polylysine-coated coverslips in a 24-well microtiter plate. Before carrying out the immunofluorescence assay the cell culture medium was discarded and the cells washed twice with PBS.

Cells were then fixed with 2% paraformaldehyde for 10 min at r.t. and the cells further washed with PBS for three times to get rid of the excess fixative.

The cells were then incubated at r.t. for 1 h in the presence of the primary anti-PSMA antibody at the concentration of 10 µg/ml. The following antibodies were used: D2/B, 7E11 (used as a well known reference antibody to an intracellular epitope of PSMA), an anti-MHC class-I antibody (as a positive control for cellular staining) and an isotypic control (negative control).

Excess antibody was eliminated by 4 washings with a 0.2% BSA solution in PBS.

Incubation with a secondary anti-mouse FITC (fluorescein)-labelled antibody (Beckman Coulter, USA) diluted 1:200 was carried out for 1 h at r.t.

After 2 further washings with PBS 2 drops of PBS/glycerol were added and the coverslip mounted on a glass slide and sealed.

The sample was then observed by a fluorescence microscope Axioskop 20 (Carl Zeiss, Germany).

The D2/B monoclonal can specifically recognize LNCaP cells (PSMA+) but cannot detect cells lacking the PSMA antigen (i.e. DU145 cells).

Example 6

Immunohistochemistry on Paraffin Embedded Tissue Samples

Sections of human prostate carcinoma embedded in paraffin were used to evaluate the recognition ability of human tumor tissues by the antibody D2/B in comparison to the already known and described antibody J591. Paraffin embedded tissues were placed in an oven at 60° C. (30 to 60 min), treated 5 times with xylol for 4 min each time, sequentially rehydrated twice in 100%, 95%, 75% ethanol for 3 min each and immersed in $H_2O$ for 5 min; to unmask the PSMA antigen the samples were then placed in a steam bath in 10 mM citrate buffer pH 6.0 for 15 min at 95° C. After 3 washings in PBS for 5 min each, incubation in PBS+3% $H_2O_2$ for 6 min and 3 further washings in PBS for 5 min each, the samples were treated with PBS+0.1% BSA for 30-40 min to saturate non-specific binding sites; incubation with the primary antibody (D2/B or J591, both at 2 μg/ml) was carried out o.n. at 4° C.; after 3 washings with PBS for 5 min each the kit EnVision Detection System HRP/DAB (Dako) was used, following the manufacturer's instructions.

Counterstaining was carried out with Gill hematoxylin for 5 sec, followed by washings with abundant H2O, and subsequently with sequential 75%, 80%, 95%, 100% solutions of ethanol and then with xylol for 4 times, 5 min each time. The slides were then mounted with resin and observed by a light standard microscope.

Example 7

Flow Cytometry

Flow cytometry allows the evaluation of important physico-chemical parameters of particles in suspension. Using a laser emission and optical detectors the system records the fluorescent light emitted by a fluorochrome (organic compound emitting fluorescent light when appropriately excited) linked to a monoclonal antibody specific for molecules expressed at the surface and/or in the cytoplasm of a cell under investigation. The signal emitted is then converted in analog/digital signals.

This technique was used to evaluate important parameters, such as:

the specificity, i.e. the ability of the antibodies obtained (D2/B and scFv D2B) to selectively bind the relevant antigen on the surface of antigen-positive cells without aspecifically binding antigen-negative cells;

the concentration of the antibody saturating the antigen sites expressed at the surface of LNCaP cells, as compared to the control antibody J591.

LNCaP and PC-3 cells cultured at 37° C. were detached from plastic surfaces with Trypsin/EDTA for 4 min at 37° C., neutralized with complete medium, washed twice with 10 ml of a cold solution of PBS/0.2% BSA by centrifugation at 1000 rpm for 5 min at 4° C. and finally 2-3×105 cells/0.5 ml were incubated with D2/B, J591 or an isotype control for 1 h at 4° C. Following two washings with 3 ml PBS/0.2% BSA at 4° C. to eliminate the excess of primary antibody, the cells resuspended in 100 μl PBS/0.2% BSA were incubated for 30 min at 4° C. in the presence of a saturating amount of a secondary antibody (approx. 1 μg/100 μl), FITC (fluorescein)-labelled goat IgG anti-mouse IgG.

At the end of the incubation time, following a further washing and resuspension of the cells in 500 μl PBS/0.2% BSA, flow cytometry analysis was carried out using a cytofluorimeter (BD FACSCanto). To detect binding of scFv D2/B a mouse anti-myc tag secondary antibody was used followed by a goat anti-mouse FITC-labelled antibody.

The parameters that were considered in the analysis were: mean fluorescence intensity (MFI) of the cells investigated and the percentage of cells found in a window comprised between channel 500 and 256.000; cells within this range were considered positive.

To verify the binding ability of the antibodies, LNCaP cells were incubated with increasing amounts of anti-PSMA D2/B or scFvD2B antibodies or with the antibody J591 of which the affinity of binding is known. With MFI values obtained a binding curve was plotted where the value yielding 100% saturation of the antigen sites corresponds to the antibody concentration where the highest fluorescence value was recorded.

Figure 4:
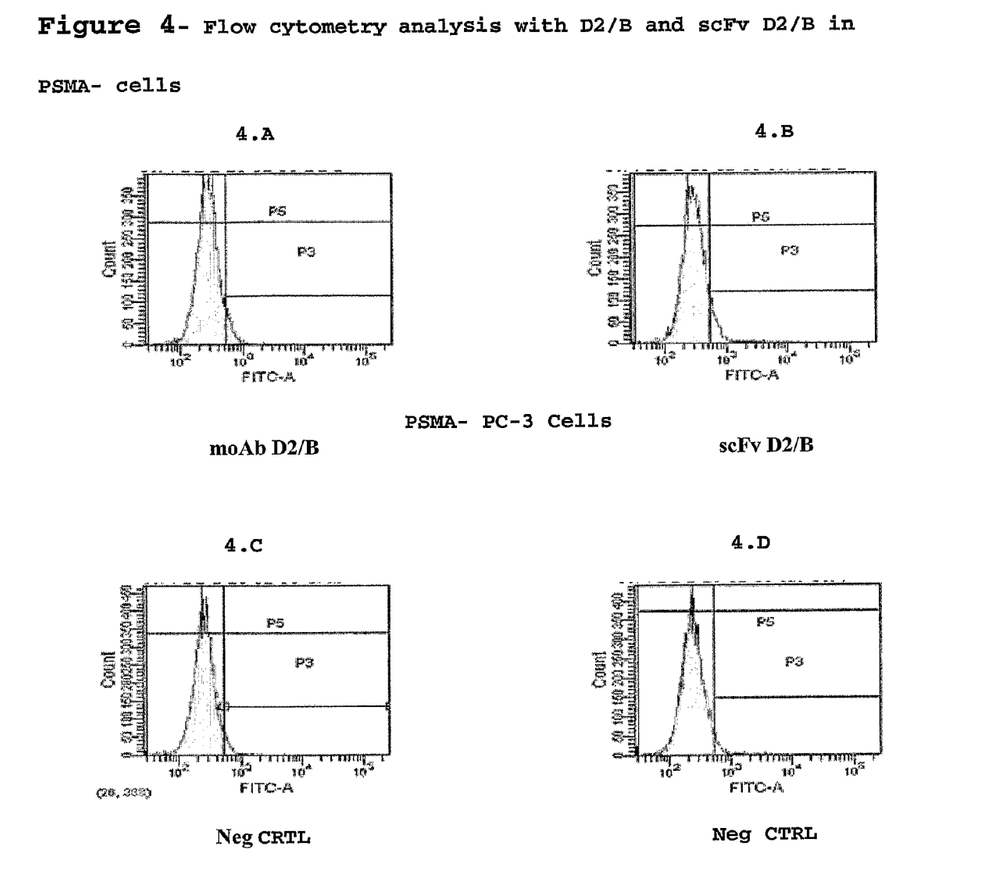

As illustrated in FIGS. 3.A and 3.B the D2/B and scFv D2/B antibodies recognize the antigen expressed on the plasma membrane at a value of MFI of approx. 8000 and 1500, respectively. In FIGS. 3.C and 3.D are reported the negative controls. Using the same technique we also evaluated the specificity of the moAb by analyzing the non-specific binding to the antigen-negative cells, PC-3 (bone metastasis of prostate carcinoma); the results, summarized in FIGS. 4.A and 4.B, show the lack of binding of the moAb D2/B and scFv D2/B, respectively. FIGS. 4.C and 4.D show the respective negative controls.

Figure 5:
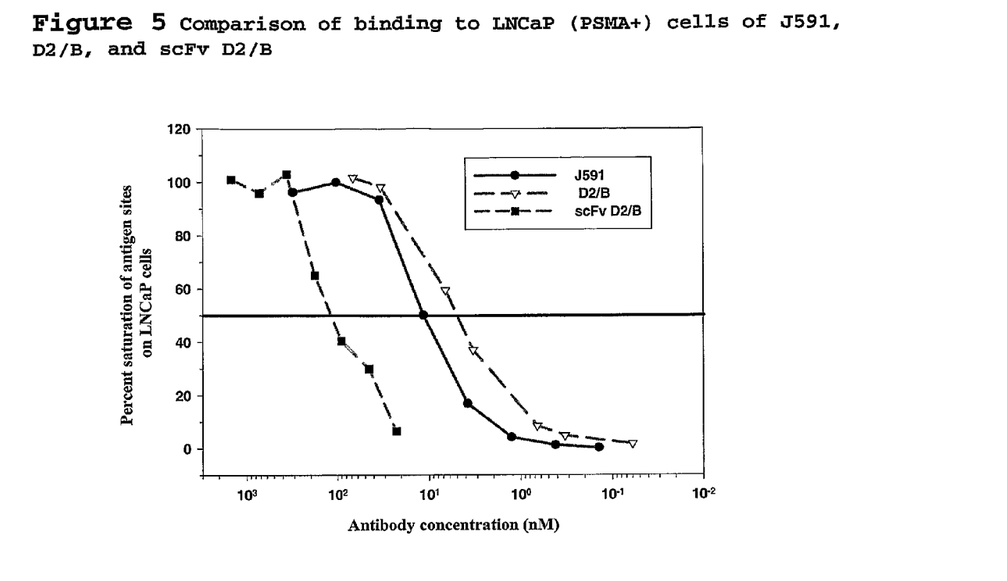
FIG. 5 shows a comparison of the binding ability to LNCaP cells (PSMA+) of Ab J591, Ab D2/B, scFv D2/B.

The concentration of J591, D2/B and scFv D2/B saturating the antigen sites (PSMA) expressed at the surface of LNCaP cells is shown in FIG. 5.

Example 8

Synthesis of Immunotoxins. Chemical Cross-Linking of RTA

The Immunotoxin synthesis has proceeded as described below.

Before conjugation the antibody D2/B was loaded onto an AffiBlue gel column to eliminate the fraction of antibodies that could bind to the matrix and which could contaminate the Immunotoxin preparations and reduce its cytotoxic efficacy. The eluted D2/B was dialyzed in PBS and derivatized with SMPT (4-succinimidyloxycarbonyl-alpha-methyl-alpha(2-pyridyldithio)toluene) dissolved at 10 mM concentration in anhydrous dimethylformamide, with a ratio IgG:cross-linker of approx. 1:2.5.

Excess cross-linker was eliminated by gel filtration on PD-10 columns (Pharmacia, Uppsala, Sweden).

The number of SH groups introduced, corresponding to the number of possible bonds linking the toxin to the antibody, was determined based on the fact that DTT, by reducing thiol groups, releases the group piridyne-2-thione which can be quantified spectrophotometrically at 343 nm. This value was comprised between 1.2 and 1.5.

Recombinant RTA, produced and purified according to a protocol described by Chignola et al. (J. Biol. Chem., 270: 23345-51, 1995) was treated with 25 mM DTT (dithiothreitol) at r.t. for 2 h to reduce cysteines and make them available to conjugation.

DTT was subsequently eliminated by gel filtration on PD-10 columns and the toxin, reduced and purified, was concentrated by Centricon-10 (Amicon, Beverly, Mass.).

Conjugation reaction to link the derivatized D2/B antibody and RTA was carried out at r.t. for 48 h.

The resulting immunotoxin was purified by gel filtration on a TSK3000SW column (Beckman, San Ramon, Calif.), with a 0.5 ml/min flow and PBS as eluting buffer.

Peaks corresponding to molecular species of 150-180 kDa (D2/B+1 RTA) and 210-240 kDa (Ab+2/3 RTA) were further purified onto AffiBlue gel, with a 150 nM-1 M salt gradient in phosphate buffer 5 mM. The toxin alone has a m.w. of approx. 30 kDa whereas the antibody has a m.w. of approx. 150 kDa.

A column of AffiBlue gel was then utilized because its matrix can bind enzymes which exploit NAD as a coenzyme or which have nucleotide sequences as substrate, like RTA; for these reasons this gel can specifically bind RTA (and antibody-RTA conjugates) while allowing the free antibody to pass through.

The fractions containing the protein of interest were pooled, concentrated with Centricon-10, dialyzed against PBS. The protein concentration was evaluated spectrophotometrically and the different pools sterilized by filtration.

Example 9

Obtainment of Immunotoxin scFv D2/B-PE40 by Gene Fusion (Nucleotide Sequence SEQ. ID. No. 5)

The sequence of scFv D2/B was cloned in a pET11d vector between Nco I and Hind III restriction sites; downstream of Hind III was inserted the nucleotide sequence coding for the PE40 toxin.

The fusion protein is produced in *E. Coli* strain BL21(DE3) pLysS previously transformed with the plasmidic vector coding for the Immunotoxin; the bacteria grown at 37° C. with agitation (225 rpm) in LB medium additioned with 0.5% glucose, 0.05% MgSO4, ampicillin 100 μg/ml, chloramphenicol 34 μg/ml, were induced at an absorbance of 0.8 at 600 nm with 1 mM IPTG final. After 3 h incubation the bacteria harvested by centrifugation at 5000 rpm are lysed by incubation and sonication in lysis buffer (Tris 20 mM pH=7.5+EDTA 10 mM+Triton-X100 1%) additioned with 0.1 mg/ml lysozyme, 0.1 mM PMSF, protease inhibitors (Roche). Inclusion bodies (IB) are harvested by centrifugation at 10.000 rpm at 4° C., these are washed twice in lysis buffer and solubilized at 20 mg/ml concentration in CAPS buffer 50 mM pH=11 additioned with N-lauryisarcosine 0.8-1.0% final and DTT 1 mM. Insoluble material was removed by centrifugation and the protein was refolded by successive dialyses. Dialysis I and II were carried out for 12 h at 4° C. in Tris 20 mM pH=8.5+DTT 0.1 mM+PMSF 0.1 mM, dialyses III and IV were carried out for 12 h in Tris 20 mM pH=8.5+PMSF 0.1 mM, dialysis V was carried out for 24 h in Tris 0.1 M pH=8.0+reduced L-glutathione 5 mM+oxidized L-glutathione 0.5 mM+L-arginine 0.4 M+PMSF 0.1 mM, dialysis VI was carried out for 24 h in Tris 20 mM pH=7.4+PMSF 0.1 mM.

The protein was then purified by 2 runs through QAE column (Bio-Rad) with a 200 ml linear 0-0.5 M NaCl gradient in Tris 20 mM pH=7.4, volume of fractions recovered was 2.5 ml.

The purity of the protein was evaluated in SDS-PAGE and identified by Western blot.

Example 10

Cytotoxicity in Monolayer Cells

The cytotoxic effect of the immunoconjugate was evaluated in PSMA-positive and PSMA-negative cells by measuring the inhibition of cell proliferation, as compared to the toxin alone.

LNCaP or PC-3 cells were seeded in 96-well microtiter plates in complete medium in amounts adequate to reach sub-confluence in control untreated wells in the 32 h of the assay.

Some wells were treated with increasing amounts of the immunotoxins D2/B-RTA (obtained by chemical conjugation using the SMPT cross-linker) or scFv D2/B-PE40 (obtained by gene fusion) or with the control immunotoxin J591-RTA (obtained by chemical conjugation with the SMPT cross-linker), other wells were treated with RTA, PE or PE40 alone, the moAb D2/B or scFv D2/B alone, for 22 h at 37° C.

The cells were then harvested on fiber filters by a cell harvester and the radioactivity incorporated was measured by liquid scintillation in a β-counter.

The cytocidal effect is expressed as a function of the incorporation of tritiated thymidine as compared to a control represented by untreated cells; results are expressed as a percent of the proliferation inhibition. The smaller the radioactive emission, the smaller the incorporation of tritiated thymidine, the bigger was therefore considered the inhibition of cell growth.

The IC50 was then calculated, i.e. the concentration of the drug which is able to inhibit 50% of the cell proliferation; this value can be easily compared with the IC50 measured using different molecules in the cytotoxicity assay.

TABLE 2

|  | LNCap PSMA+ ng/ml | PC-3 PSMA− ng/ml |
| --- | --- | --- |
| J591-smpt-RTA | 7.4 | >1.260 |
| D2/B-smpt-RTA | 21 | >16.800 |
| scFv D2/B-PE40 | 1.3 | >6.500 |
| moAb D2/B | >6.000 | >6.000 |
| scFv D2/B | >3.300 | >3.300 |
| PE toxin | 2.4 | 3.4 |
| PE40 toxin | 1.950 |  |
| RTA toxin | 12.000 | 9.000 |

Example 11

Monobiotinylated scFv D2/B

Monobiotinylated scFv D2/B were obtained by cloning the scFv molecule between NcoI and NotI restriction sites; in the cloning vector in 3' with respect to the NotI site were cloned successively: a sequence coding for a domain derived from the hinge region of IgA, a sequence coding for a peptidic stretch named BAD (Biotin Acceptor Domain), and a sequence coding for a cleavable fragment recognized by the proteases Enterokinase and Factor X. The hinge region of IgA is a spacer between scFv and BAD domain, which is monobiotinylated in a reaction catalyzed by the enzyme BirA. The production of the biotinylated protein was carried out in bacteria transformed with the plasmid of interest and are able to biotinylate the BAD site; by IPTG induction and addition of free biotin to the culture medium the protein under investigation is obtained; this includes the scFv domain endowed with the desired specificity and one single biotin molecule.

The protein scFv-biotin was purified on a NiNTA gel under partially denaturing conditions to facilitate the exposure of the N-terminal 5-His tag and the binding to the column. The purity of the protein was analyzed by SDS-PAGE whereas its identity was confirmed by Western blotting using HRP-labelled secondary antibodies to the scFv and to the His tag.

Functional properties of the biotinylated scFv was then assayed by FACS analysis carried out with PSMA+ (LNCaP) and PSMA− (PC-3) cells.

The MFI in LNCaP cells is 161, 728 and 314 for the negative control (avidin-FITC alone), for chemically biotinylated D2/B antibody and the enzymatically labelled scFv-D2/B, respectively, whereas the MFI values obtained with PC-3 cells are 132, 151 and 180, respectively.

Example 12

Figure 6:
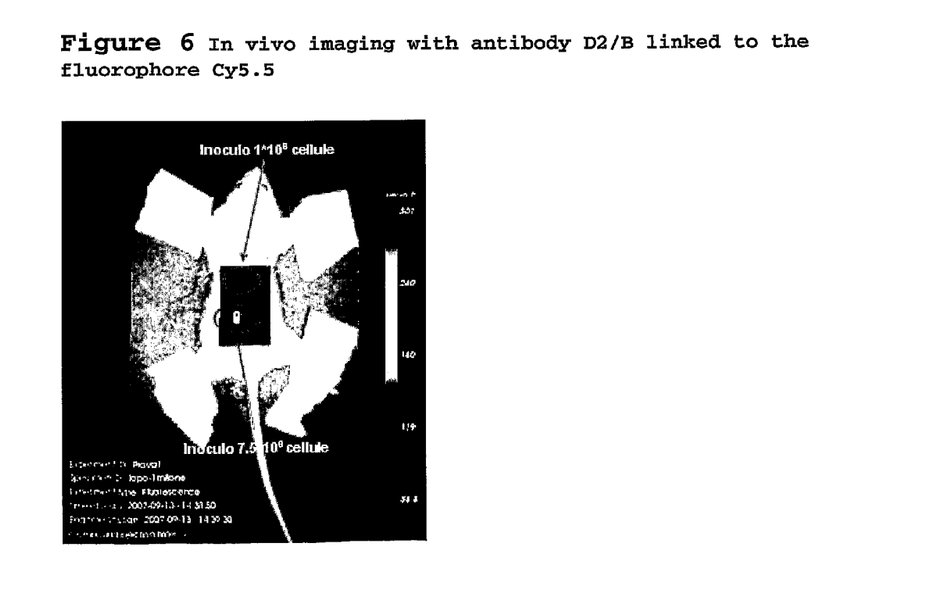
FIG. 6 shows an in vivo imaging with Ab D2/B conjugated with fluorophore Cy5.5.

Example of In Vivo Imaging Using D2/B Antibody Labelled with Fluorescent Tracers To address the possibility of applying in vivo imaging techniques based on the use of D2/B or scFv D2/B antibodies labelled with fluorescent tracers, immunodeficient SCID mice were inoculated with LNCaP cells pre-treated in vitro with D2/B antibody linked to the fluorochrome Cy5.5, according to the manufacturer's instructions. This assay has allowed to trace a s.c. implant of 7.5×106 PSMA+ cells, but we have good indications that lower numbers of cells can be identified (i.e. down to 106 cells). FIG. 6.

Example 13

Example of Cross-linking to a Radioactive Isotope

The choice of the chelating agent used to derivatize an antibody is dependent upon the choice of radionuclides that need to be conjugated to the antibody itself; additionally, the chelating substance must be endowed with an available functional group exploitable for linking to the antibody. For instance the compound DOTA can be directly cross-linked to the antibody via one of the 4 carboxyl groups available; the antibody is concentrated, washed with 1% DTPA (pH=5.0), dialyzed in 0.1 M phosphate buffer (pH=7.0) and reacted with active esters of DOTA. Active esters of DOTA are created by dissolving 0.361 mmol (146 mg) and 0.313 mmol (36 mg) of N-hydroxysuccinimide in 2 ml of H2O and adjusting the pH to pH=7.3 with NaOH prior to the addition of 10 mg of 1-ethyl-3-(3-dimethylaminopropyl)carbodiimide. The reaction mixture is cooled on ice for 1 h before being added to the antibody to be derivatized. The resulting DOTA-antibody conjugate is separated from excess DOTA and other reactants by gel filtration (PD-10 columns) or by centrifugation (Amicon concentrators) using a 0.3 M ammonium acetate solution. Radiolabeling of DOTA with 111In is achieved by adding 111InCl3 in 0.01 M HCl to the 0.3 M acetate solution of DOTA-Ab.

After 20 min the reaction mixture is separated by Biogl-P6 columns equilibrated in with 1% HSA-PBS. The amount of free radioisotope is evaluated by TLC chromatography.

---

The invention claimed is:

1. An isolated D2/B monoclonal antibody or antigen-binding fragment thereof, wherein the antibody selectively binds prostate specific membrane antigen (PSMA) and is encoded by variable region nucleotide sequences comprising SEQ ID NO: 1 and 2.

2. A scFv fragment of a D2/B antibody wherein the fragment is encoded by a sequence comprising the antigen-binding variable regions VH and VL of SEQ ID NO:3.

3. The isolated monoclonal antibody or antigen-binding fragment thereof according to claim 1, characterized by binding PSMA in its native form on the surface of prostate tumor cells.

4. A conjugate comprising an isolated monoclonal antibody acccording to claim 1 or scFV fragment according to claim 2, conjugated with an active ingredient selected from the group consisting of a labelling agent, a cytotoxic agent and a carrier.

5. The conjugate according to claim 4, characterized in that said labelling agent is a radionuclide or fluorescent nanoparticles.

6. The conjugate according to claim 4, characterized in that said labelling agent is selected from the group consisting of $^{188}$Re, $^{131}$I, $^{125}$I, $^{123}$I, $^{187}$Re, $^{111}$In, $^{90}$Y, $^{99}$mTc, and $^{177}$Lu.

7. The conjugate according to claim 4, characterized in that said cytotoxic agent is PE40, the ricin A chain, saporin or diantin.

8. A scFv D2/B-PE40 conjugate encoded by SEQ ID NO:5.

9. The conjugate according to claim 4, characterized in that said carrier is biotin or nanoparticles.

10. A pharmaceutical composition comprising an isolated monoclonal antibody or antigen-binding fragment thereof according to claim 1.

11. A pharmaceutical composition comprising a conjugate according to claim 4.

12. A method of treating or diagnosing a tumor comprising contacting a PSMA+ tumor with a conjugate according to claim 4.

13. The method according to claim 12, characterized in that said tumor is a prostate tumor.

14. A method for inhibiting PSMA-associated proliferation of a tumor of any histotype comprising contacting the tumor with a conjugate according to claim 4.

* * * * *

UNITED STATES PATENT AND TRADEMARK OFFICE
CERTIFICATE OF CORRECTION

| | | |
|---|---|---|
| PATENT NO. | : 8,703,918 B2 | Page 1 of 1 |
| APPLICATION NO. | : 12/989316 | |
| DATED | : April 22, 2014 | |
| INVENTOR(S) | : Colombatti et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 761 days.

Signed and Sealed this
Fifteenth Day of December, 2015

Michelle K. Lee
*Director of the United States Patent and Trademark Office*